United States Patent [19]

Honeycutt et al.

[11] Patent Number: 4,793,330

[45] Date of Patent: * Dec. 27, 1988

[54] ORTHOPEDIC CAST SYSTEM

[75] Inventors: Travis W. Honeycutt, Irvine, Calif.; Barry D. Setzer, Hickory, N.C.

[73] Assignee: Isopedix Corporation, Irvine, Calif.

[*] Notice: The portion of the term of this patent subsequent to Mar. 4, 2003 has been disclaimed.

[21] Appl. No.: 746,351

[22] Filed: Jun. 18, 1985

[51] Int. Cl.$^4$ .............................................. A61F 5/04
[52] U.S. Cl. ..................... 128/90; 428/254; 524/850; 526/298; 523/105
[58] Field of Search ............ 128/90; 524/850; 526/298; 428/36, 254; 523/105

[56] References Cited

U.S. PATENT DOCUMENTS

| | | |
|---|---|---|
| 2,720,097 | 10/1955 | De Mond . |
| 2,765,332 | 10/1956 | Coover et al. .................. 526/298 |
| 3,064,456 | 11/1962 | Bird . |
| 3,097,644 | 7/1963 | Parker . |
| 3,178,379 | 4/1965 | Wicker et al. .................. 524/850 |
| 3,215,137 | 11/1965 | Laakso ............................. 128/90 |
| 3,254,111 | 5/1966 | Hawkins et al. ............... 526/298 |
| 3,301,018 | 1/1967 | Knohl . |
| 3,305,911 | 2/1967 | Chapman . |
| 3,527,841 | 9/1970 | Wicker et al. .................. 526/298 |
| 3,683,903 | 8/1972 | Fox et al. .......................... 128/90 |
| 3,699,127 | 10/1972 | O'Sullivan et al. ............. 524/850 |
| 3,782,390 | 1/1974 | Johnson ............................ 128/90 |
| 4,007,748 | 2/1977 | Matranga et al. . |
| 4,048,818 | 9/1977 | Cueman . |
| 4,052,282 | 10/1977 | Kubushiro . |
| 4,105,715 | 8/1978 | Gleave ............................. 526/298 |
| 4,214,578 | 7/1980 | Glarakakos et al. ............ 128/90 |
| 4,226,230 | 10/1980 | Potts ................................ 128/90 |
| 4,238,522 | 12/1980 | Potts . |
| 4,286,586 | 9/1981 | Potts . |
| 4,427,003 | 1/1984 | Fennimere et al. ............. 128/90 |
| 4,477,607 | 10/1984 | Litke ............................... 524/850 |
| 4,502,479 | 3/1985 | Garwood et al. . |
| 4,574,097 | 3/1986 | Honeycutt ....................... 428/36 |

*Primary Examiner*—John D. Yasko
*Assistant Examiner*—Mark F. Colosimo
*Attorney, Agent, or Firm*—Malcolm B. Wittenberg

[57] ABSTRACT

A kit for the application of orthopedic casts and splints which is completely self-contained requiring no ingredients other than those contained within the kit. Each kit contains a fabric with a hardening quantity of an acyanoacrylate monomer containing composition which, when applied to the fabric, results in an orthopedic cast or splint capable of immobilizing an injured appendage.

100 Claims, 2 Drawing Sheets

U.S. Patent  Dec. 27, 1988  Sheet 1 of 2  4,793,330
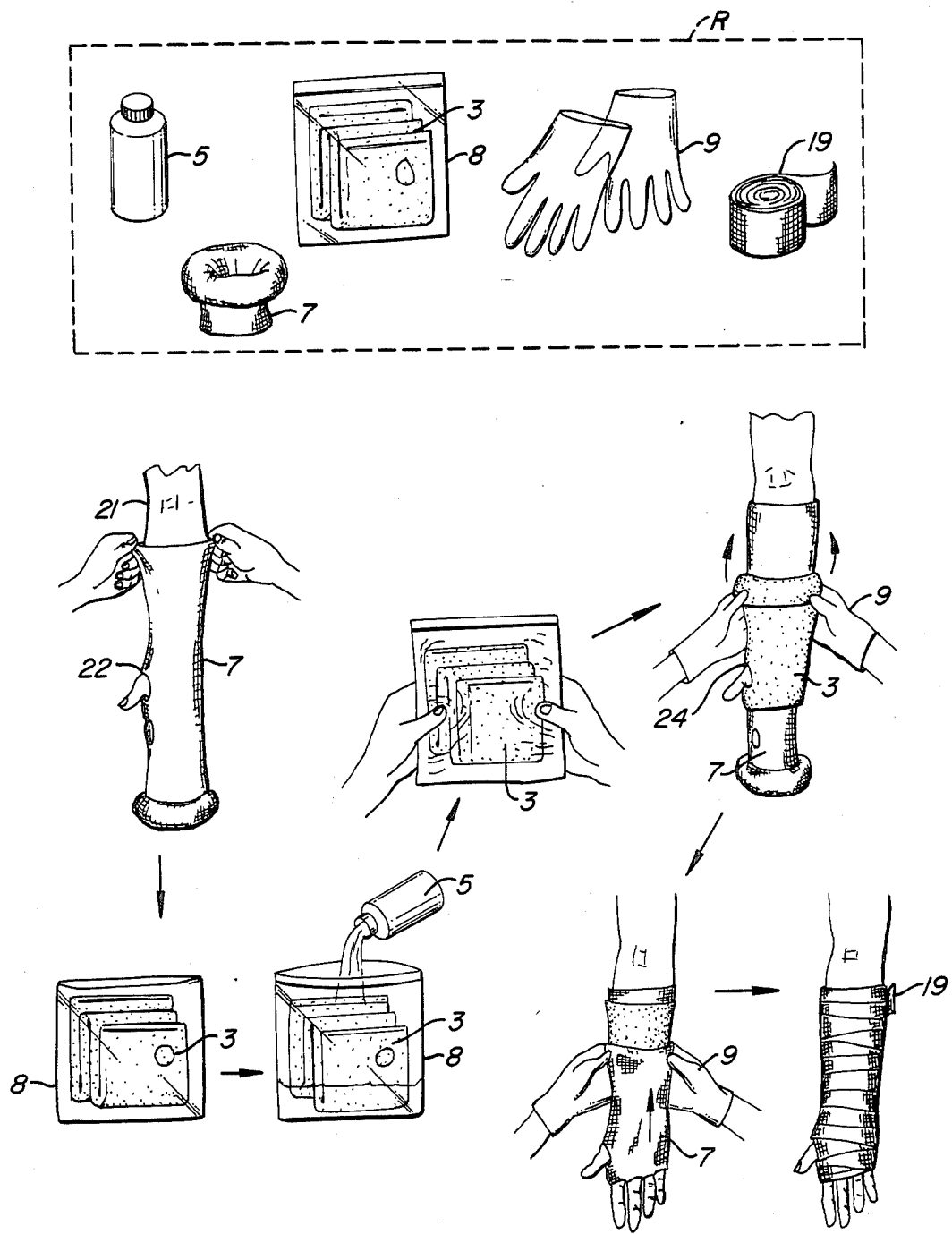
FIG._1.

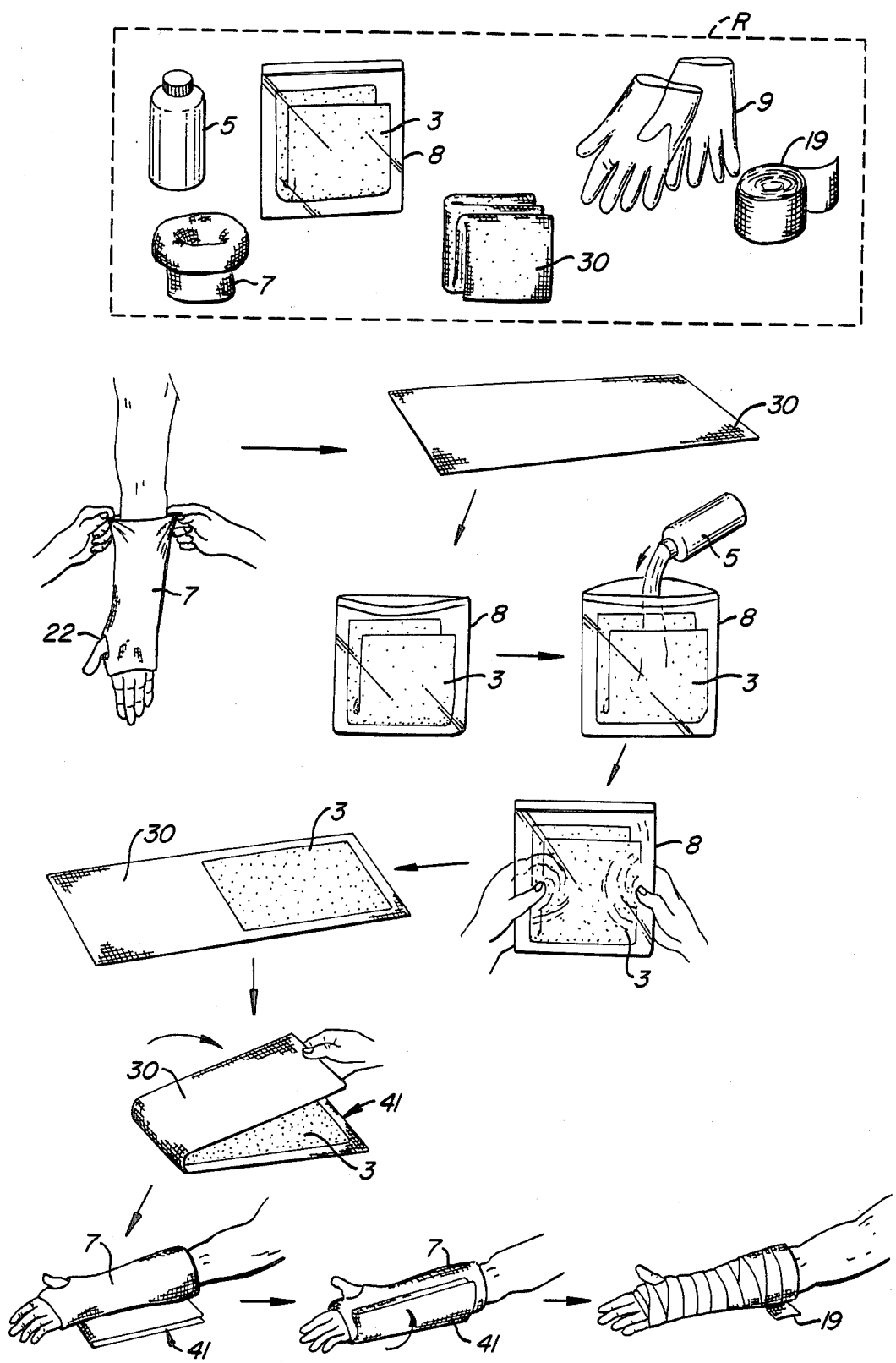
FIG._2.

ORTHOPEDIC CAST SYSTEM

TECHNICAL FIELD OF INVENTION

The present invention deals with various materials which can be used to make kits for fabricating orthopedic casts and splints. The kits are designed for use by doctors and other medical professionals who will view them as completely self-contained products capable of providing an orthopedic cast or splint which can readily be used to immobilize an injured appendage without the need to resort to any ingredients or aids not contained within the kits themselves.

BACKGROUND OF THE INVENTION

Current orthopedic practice employs basically the same processes and materials for immobilizing an extremity which have been used for years. Regarding splinting and casting appliances, there are several different types of approaches currently being practiced. These can generally be characterized as various plaster composites as well as malleable aluminum plates and rods and other devices such as sticks, boards and inflatable balloons and cardboard materials.

Plaster-based composites are calcium sulfate impregnated textile fabrics such as cotton cheesecloth or gauze. These plaster-based splinting and casting orthoses must be configured in the presence of the patient and are built up by combining either sheets or rolls of plaster-based composite materials in gauze or stockinettes followed by elastic wraps. These materials are quite fragile within the first few hours of construction and are subject to easy breakage. Even upon drying, they are very heavy and suffer from a number of disadvantages, such as a lack of breathability, and are incapable of producing an orthopedic device which is anything but radiolucent. Further, plaster of paris is, by its very nature, hydrophilic which means that moisture is retained within the cast which in turn provides an ideal breeding ground for bacteria and fungi on sites next to the skin.

Due to the inherent disadvantages present in the use of plaster of paris materials, recent interest has been focused towards suitable replacements. As illustrative, water dip fiberglass/urethane resins splints and casts are entering the market but are not in general use. Some medical professionals have expressed concern about a lack of moldability of such materials as the inelasticity of fiberglass/urethane materials is well-known. These characteristics are translated into a spiral wrapping which tends to be extremely brittle, resulting in a flare up of "pressure sores" commonly experienced by the user of such orthoses unless the medical practitioner is extremely versed in their application. This inherent stiffness also means that fiberglass-based casting tapes are virtually impossible to mold onto the injured appendage.

U.S. Pat. Nos. 3,089,486 and 3,908,644 teach the use of acrylic monomers, i.e., having the general structure $H_2C=CR_1R_2$ wherein $R_1$ is usually a hydrogen atom or a methyl group and $R_2$ is usually a carboxylic acid group or its ester. These monomers are polymerized to produce hardenable members; however, systems employing these materials are fraught with disadvantages. Being free radical polymerizable, an external source of free radicals is needed as well as a reaction initiator such as ultraviolet light. Further, the monomers are skin penetrants and thus barriers are absolutely necessary to protect the user from these potentially toxic materials. Their shortcomings are further manifested by the fact that most if not all acrylic monomers exhibit a strong and objectionable odor which makes them unsuitable as major components for orthoses. Lastly, such monomers characteristically do not polymerize "rock" hard, take too long to polymerize to make such casting systems convenient to use, and traditionally employ flammable solvents resulting in a rather hazardous system.

U.S. Pat. Nos. 4,376,438 and 4,411,262 disclose resin systems which can be characterized as "condensation comonomers," i.e., diisocyanates and polyols. Such monomers are usually employed by preparing a premix of these materials with a catalyst in the absence of moisture and air. The catalysts generally employed are such things as mercuric or tin amine or imine, all of which are potentially toxic. In use, diisocyanate-based systems require a water dip to unblock the stabilized monomer.

It is one of the objects of the present invention to provide a self-contained kit which eliminates the need for the use of any external ingredient, such as water, not contained in the kit.

It is a further object of the present invention to develop a casting system which could be provided in a completely self-contained kit which is lighter and easier to use than prior plaster and fiberglass casts, would require only modest expertise to use, and yet exhibit excellent moldability, be completely X-ray transparent, substantially water resistant, and develop less of an exotherm during hardening or setting.

It is still a further object of the present invention to provide a cast or splint which exhibits a relatively high modulus of elasticity enabling the orthosis to absorb stress by slight bending rather than cracking, a result which is most uncharacteristic of plaster and fiberglass orthopedic members.

It is yet another object of the present invention to provide a cast or splint system which is available in a completely self-contained kit form while producing splints and casts having those advantages over the prior art as recited previously.

It is still another object of the present invention to provide cast and splint members as well as methods for their fabrication and use wherein the cast and splint members are significantly more water-repellant and resistant than plaster or fiberglass cast materials and are of a lighter weight and thus when wet, dry considerably quicker than their prior art counterparts. Significantly, the casts and splints manufactured pursuant to the present invention are considerably more porous than prior orthoses which should aid in breathability and thus promote a healthier skin condition during long-term usage.

It is finally an object of the present invention to provide cast and splint systems in which the hardening agent would autocatalytically cure at ambient conditions without resorting to externally applied heat, pressure, enhancers, oxidizers, ultraviolet light, peroxides or other initiators or promoters.

These and further objects of the present invention will be more fully appreciated when considering the following description and appended drawings wherein:

FIG. 1 shows a step-by-step method for employing a kit for the fabrication of a cast pursuant to the present invention.

FIG. 2 is similarly a step-by-step illustration of the use of the kit for fabricating a splint pursuant to the present invention.

SUMMARY OF THE INVENTION

The present invention deals with related materials which can be combined to form kits for the application of casts and splints useful in the immobilization of injured appendages. Also embraced as part of the present invention are methods for employing the kits in fabricating the various orthoses as well as the final products which result therefrom.

In each instance, the various species of the present invention have in common the use of a hardenable fabric which, pursuant to various preferred embodiments disclosed hereinafter, is capable of containing various ingredients for "fine tuning" the hardening process. Additionally, the present invention, in all of its various embodiments, employs an α-cyanoacrylate monomer containing composition for application to the fabric as the hardening agent.

Lastly, the present invention contemplates the use of a barrier fabric which can be employed between the skin of the user and the hardenable fabric which exhibits high thermal capacitance and low thermal conductivity to protect the user in the event that the polymerization or hardening reaction, being exothermic in nature, produces an uncomfortable warmth. The barrier fabric is taught as being useful as a preferred embodiment herein as well as in the casting and splinting systems of the prior art.

DETAILED DESCRIPTION OF THE INVENTION

As previously noted, the present invention contemplates the use of fabric which is capable of supporting a hardening quantity of an α-cyanoacrylate monomer containing composition. The fabric, designated as element 3 of FIGS. 1 and 2 can be configured in the shape of tubular members (FIG. 1) or flat sheets (FIG. 2) or even as tape-like members for the building of the various orthopedic devices.

To facilitate application, when the fabric is tubular, it ideally should be able to stretch at least once its at-rest width which would greatly enhance the conformance and moldability of the structure.

Keeping in mind that the fabric is the structural material that is intended to co-act with the α-cyanoacrylate monomer containing composition to provide structural integrity which is, of course, a necessary requisite for casting and splinting orthoses, the core should be made from a fiber or combination of fibers which, when brought in contact with the monomer-containing composition, act in concert with the monomer to produce a hard composite member. Yet, for casting and splinting applications, this must occur nonspontaneously in the sense that there must be approximately 1 to 20 minutes of working time prior to immobilization to enable the medical practitioner to conform the cast or splint to the appendage.

Subject to various considerations noted below, it is generally believed that the fabric can be comprised of a member selected from the group consisting of a textile ribbed knit, a woven fabric, a jersey, a tricot and an interlock knit as well as nonwovens such as felts and paper structures. Textile ribbed knits are particularly appropriate for the cast application for, most often, the cast fabric would be configured in the shape of a tube in which a certain degree of stretch and recovery therefrom is an important consideration.

Regardless of the stitching technique employed in configuring the fabric, it is important to select the appropriate fiber to ensure that the technician or physician applying the cast is provided with ample time to apply the α-cyanoacrylate monomer containing composition to the fabric and is subsequently provided sufficient time to configure the coated fabric to the shape of the injured appendage. Suitable fabrics should be relatively free of water, alcohols, sugars, polyols, amines, imides, amides, and other nucleophiles which tend to promote the too rapid polymerization of the α-cyanoacrylate monomer. Suitable fabrics include such things as polynosics which include cotton, rayon and cellulose esters, polyesters, polyamides such as nylon, spandex, polyacrylics, polyolefins, polyaramids, fiberglass and carbon. Other natural and synthetic fibers can also be chosen as long as the various nucleophiles which promote polymerization are kept at appropriate levels to ensure that the practitioner has sufficient time to fabricate and apply the orthopedic member. Modest reaction rates are further desired as they tend to spread heat generation over time and produce a harder composite due to ordered polymerization and chain packing. Chaotic reaction rates tend to cause over-heating which results in a softening of the fabric due to its thermal plasticity.

As illustrative, it was found that hardened composites were created more readily with α-cyanoacrylate monomer containing compositions when applied to polynosic fibers as compared to polyesters or nylon. Polynosics were found to have a higher moisture regain as compared to polyesters and nylon. Knowing that moisture catalyzes α-cyanoacrylate monomers, this result is not surprising.

In order to control the speed of polymerization, it is the intent of the present invention, as a preferred embodiment, to remove substantially all of the water, alcohols and amines from the fabric by means of, for example, subjecting the fabric to desiccation. Thereupon, the fabric can be placed in a sealed pouch for inclusion in the kit.

In preparing the fabric for use herein, it is the intent to include a small amount of a Lewis base in the fabric in order to cure the monomer-containing composition. As a general rule of thumb, the more Lewis base present, the faster the rate of polymerization. Therefore, sufficient Lewis base should be included to provide for approximately 1 to 20 minutes of time prior to hardening of the orthopedic member. More specifically, it is desirable to have approximately 1 minute of work time before any noticeable hardening occurs and 2 to 4 minutes of set time when significant stiffening is noticeable while sufficient workability is provided to ensure conformance of the orthosis with the injured appendage.

EXAMPLE 1

Approximately 28 grams of a 100% cotton 18-gauge rib-knit tubular fabric was wet with approximately 70 grams of ethoxyethyl α-cyanoacrylate monomer which was inhibited with approximately 130 ppm $SO_2$ available from Toagosei Chemical Industries, Ltd. as Product No. 811. The cotton member was placed in a plastic bag together with the α-cyanoacrylate monomer and, as the components were combined, several hot spots formed on the cotton fabric which could not be rewet, evidencing advanced polymerization of the monomer. A useful cast could not be made from this material.

EXAMPLE 2

The cotton tube of Example 1 was wet with approximately 69.5 grams of the same monomer. However, prior to application of the monomer, the fabric was dried under vacuum for 1 hour at 100° C. The sample was then cooled to room temperature and placed in a sealed container. Upon wetting the cotton member with the monomer-containing composition, no significant heat buildup was detected emanating from the plastic pouch. The coated fabric was applied to an appendage and only slight warming during application was discernable by the applicator. The orthosis hardened in approximately 3 minutes and was completely cured in approximately 10 minutes.

EXAMPLE 3

A 69 gram sample of a three-layered, 18-gauge rib-knit polyester fabric was dried by heating under vacuum as in Example 2, above. Approximately 172.5 grams of Toagosei's ethoxyethyl α-cyanoacrylate monomer was added to the polyester sample which was dried under heat and vacuum in a manner identical to that employed in Example 2. Significant polymerization of the monomer was not detected even after 30 minutes. Upon the expiration of a 24-hour period after adding the monomer to the polyester fabric, the composite was hard which was probably due to hydroscopic moisture in the air which initiated polymerization.

EXAMPLE 4

The polyester-cyanoacrylate monomer containing composition as disclosed in Example 3 was used once again with the distinction being that the polyester fabric was first washed in a solution of 90% water, 10% acetone (by weight). After thoroughly wetting the polyester in the water/acetone bath, the fabric was squeeze-dried and then desiccated by heating under vacuum for 30 minutes at 100° C. The sample was then immersed in a 0.25% (by weight) polyethylene imine solution to a 100% (by weight) pickup and thereafter dried.

Upon contact of the cyanoacrylate-monomer containing composition with the treated polyester, polymerization occurred too rapidly to enable the medical practitioner to employ the fabric/cyanoacrylate monomer combination as a commercially viable orthopedic member. However, when the sample was washed in a 0.1% solution of polyethylene imine and subsequently dried, polymerization was sufficiently slow such that the composite was commercially viable.

As is readily apparent, it is possible to employ a wide range of fibers in carrying out the present invention, as long as the proper "stimulus" is provided to ensure the appropriate rate of polymerization—broadly, the orthopedic member should exhibit significant stiffness after approximately 1 to 20 minutes after the monomer and fabric support have engaged one another, and, more preferably, substantial immobilization should occur between 1 to 4 minutes after application of the α-cyanoacrylate monomer containing composition to the fabric. As such, fibers including cotton, rayon, cellulose acetates, glass, polyesters, nylon, polyacrylics, polyolefins, polyaramids and carbon can generally be employed.

It has been found that if polymerization occurs too rapidly, either because of an inordinately high concentration of water or Lewis base, polymerization can be somewhat inhibited by the application of a inhibiting quantity of cellulose acetate and its homologs as well as polymethyl methacrylate and ε-polycaprolactone. Such materials, in effect, block engagement between the cyanoacrylate monomer and fabric, but are soluble in the cyanoacrylate monomer containing composition. As such, although the above-recited materials provide a blocking function, they are soon solubilized into the monomer-containing composition allowing polymerization to then occur at a point in time which has given the medical practitioner sufficient opportunity to apply the orthopedic member and mold it to the injured appendage.

EXAMPLE 5

Two samples of 18 cut 100% cotton rib knot stockinettes, each 3 inches wide, were immersed in a 7.5% by weight solution of cellulose acetate butyrate (CAB) in acetone. The stockinettes are available from Brecon Knitting Mills while the cellulose acetate butyrate solution is sold by Eastman Chemical Products, Inc. under the designation 500-1.

The first sample stockinette weighed approximately 22.5 grams prior to immersion in the CAB solution. After immersion, followed by room temperature drying for one hour and desiccation at 100° C. under a vacuum of 22 inches of Hg for about 20 minutes, the sample weighed 24.1 grams. The "pick up" of CAB was thus approximately 7.11% by weight.

The first stockinette was exposed to atmospheric conditions at a temperature of about 17° C. for a period of about 24 hours resulting in a moisture regain of approximately 2.93%. The stockinette was then used to make a splint by treating it with a solution containing an α-cyanoacrylate monomer containing composition inhibited with 25 ppm $SO_2$. The hardenable resin was used in an amount approximately 2.5 to 1 based upon the weight of the stockinette. It was observed that the stockinette wet out well as no dry spots were observed. After wet out, it was noted that the hardening of the fabric began in about 2 minutes and the orthosis became completely immobile in an additional 2 minutes. The maximum temperature which was reached during the polymerization reaction was about 102° to 104° F. All of these values point to an acceptable product fully worthy of commercialization.

The second sample stockinette weighed 24.75 grams before treatment with the cellulose acetate butyrate solution and 26.6 grams after treatment and desiccation. The resultant "pick up" of CAB was thus approximately 7.47% by weight.

The second stockinette was then sealed in a polypropylene bag and, after a 24 hour period, was used as a splint using the same monomer to fabric ratio as noted as above. As above, an excellent orthosis was produced as the fabric wet easily and was workable, before hardening, for about 10 minutes. Also, the fabric reached a maximum temperature of only 100° F. during polymerization which is well within acceptable limits.

From the above example, it is plainly apparent that the use of barrier materials on the fabric to control the rate of polymerization can be quite useful. The barrier materials should all be characterized as being soluble in the α-cyanoacrylate monomer containing solution and include cellulose acetate and its homologs such as cellulose butyrate and cellulose acetate butyrate as well as polymethylmethacrylate, and ε-polycaprolactone in quantities of approximately 0.1% to 10% by weight. With the use of such barrier materials, one is able to reduce the amount of inhibitor while maintaining low exotherm profiles during polymerization and substantially eliminate hot spots. The barrier materials also minimize moisture regain when the fabric is exposed to atmospheric conditions which, again, substantially contributes to a controlled polymerization reaction.

The yarn size generally chosen for the fabric support as the cast or splint core is in the range of 0.5 singles to 100 singles cotton count and, more preferably, 4 singles to 50 singles in the cotton count range and, most desirably, 8 singles to 30 singles. The yarn can be employed singly or in plies thereof.

As a further preferred embodiment, it is deemed desirable to build some stretch or elasticity into the fabric support when employed as a cast, particularly when configured in a tubular form. As such, in addition to the various yarns described previously, it is advantageous to employ a second yarn, such as a stretch yarn, which maintains structural integrity of the tubular cast fabric prior to the application of the fabric onto the appendage and prior to the impregnation of the cast core with the resin matrix. The stretch yarn can be woven or blended as a composite. It can be a true elastic such as synthetic or natural rubber or a synthetic spandex material whether urethane derived or polyester derived. The synthetic elastic yarns such as spandex are usable in sizes 20 to 1200 denier but more preferably between 30 to 200 denier and most preferably between 40 to 70 denier. These elastic yarns may be supported with coverings to give them added strength and workability as needed. Typical products sold under the trademark Lycra ® available from Dupont and Glospan ® available from Globe Manufacturing Co. have been found to be perfectly adequate. Regarding natural rubber or synthetic rubber yarns, it has been found that, broadly, a size of 200 to 44 gauge and, more preferably, between 110 to 90 gauge and, most desirably, approximately 100 gauge yarn can be embodied in the cast fabric core. Such materials are available from Globe Manufacturing Co.

Further, the elastic component may be a non-true elastic, that is, a product which does not change its circumferential diameter as it is stretched. In other words, non-true elastics are textured materials such as textured nylon or polyester which are known in the textile trade as stretch-textured yarns and are usable in the present invention, broadly, in sizes having yarn counts 1/40 to 1/1000 denier and, more preferably, 1/70 to 1/600 denier and, most preferably, 1/150/68 filament count. Such materials are available from Burlington Industries as well as from Macfield Texturing.

Contained within each kit will be a quantity of what will commercially be known as casting gel or resin matrix contained in plastic bottle 5 (FIGS. 1 and 2). As previously indicated, a hardening quantity of an α-cyanoacrylate monomer containing composition is intended to represent the casting gel for all embodiments of the present invention.

As preferred embodiments, α-cyanoacrylate monomer containing compositions should be selected which are low or nonodorous. The lower alkyl substituted α-cyanoacrylates such as methyl and ethyl substituted materials are quite reactive and produce hard composites when employed with the fabric described previously but, unfortunately, these products are quite odorous and their vapors tend to cause extreme eye irritation. Even the higher alkyl esters with lower vapor pressure, such as propyl, butyl, pentyl, hexyl and so forth, still produce an odor which most people would consider objectionable, particularly when exposure is made in close proximity to the patient which, of course, is the environment in which the present invention is intended to reside.

With the above-recited constraints in mind, the casting gel intended for use herein can generically be described as comprising a compound of the general formula:

$$H_2CC(CN)COOR_1$$

wherein $R_1$ is a member selected from the group consisting of alkyl, alkene, alkylalkoxy, furfuryl, aromatic and cycloalkyl groups and mixtures thereof. Preferably, $R_1$ is a member selected from the group consisting of methoxyethyl, ethoxyethyl, isopropoxyethyl, propoxyethyl, t-butoxyethyl, n-butoxyethyl, and iso-butoxyethyl and mixtures thereof. Most preferably, the alkoxy esters which exhibit low vapor pressures have been determined to be useful in practicing the present invention. The following example is considered illustrative.

EXAMPLE 6

A forearm cast orthosis was prepared by providing a three-layered cotton rib-knit fabric configured in the shape of a tube weighing approximately 29 grams. The patient was first fitted with a barrier fabric of rib-knit polypropylene also configured in the shape of a tube. The polypropylene barrier was rolled into a donut shape and unrolled onto the patient's forearm in the area to be rendered immobile by the orthosis.

The cotton fabric was mixed with approximately 72.5 grams of ethoxyethyl α-cyanoacrylate monomer by pouring the casting gel into a plastic bag containing the cotton fabric. The monomer was worked into the cotton fabric for approximately 2 minutes to ensure that complete wetness was achieved. The fabric was then rolled into a donut shape and unrolled onto the patient's forearm in the area covered by the barrier fabric. The case was set in approximately 6 minutes and cured in approximately 15 minutes while neither the medical technician nor patient noticed any objectionable odor. Skin temperatures were measured continuously, and a peak temperature of 108° F. was recorded. This was considered most satisfactory and did not result in any particular discomfort on the part of the patient.

In view of the fact that the α-cyanoacrylate monomer containing composition must "wet" the cast or split fabric, it is important to provide a hardenable composition which exhibits the appropriate viscosity. Generally, viscosities in the rang of 1 to 20 cps are acceptable while from 1 to 5 cps are most desirable, and compositions exhibiting viscosities between 1 to 3 cps clearly represent the most preferred embodiment of the present invention. The viscosities in each instance were measured at 20° C. on a Brookfield viscometer using a no. 4 spindle.

Previous indication was made that water, alcohols and amines should be removed from the polymerizable monomer-containing composition as these materials destabilize the monomer and generally tend to cause hardening of the cast or splint members too rapidly to enable the medical practitioner to thoroughly wet the fabric and apply it to the appendage. Broadly, α-cyanoacrylate monomer containing compositions can tolerate something less than approximately 3% water and approximately 2% alcohol, depending upon the specific cyanoacrylate monomer being employed. Ideally, one should try to achieve approximately 0.01% or less water and approximately 0.01% or less alcohol.

Various Lewis acids can be employed as inhibitors for stabilizing the α-cyanoacrylate monomer containing compositions. Stability is important particularly when the various compositions are enclosed in kit form where the various kits are intended to exhibit extending shelf life prior to usage.

The most practical Lewis acids for use as stabilizers are the aromatic sulfonic acids such as those disclosed in U.S. Pat. No. 4,321,180 as well as $SO_2$, the latter material being introduced to the composition as a gas which is solubilized in the liquid monomer-containing casting gel. The amount of inhibitor which is used depends to a large degree on the intended shelf life of the product as well as on the amounts of water and alcohols present in the product which, as indicated previously, tend to destabilize the composition. Broadly, it is intended that a Lewis acid inhibitor be employed between approximately 15 to 500 ppm, while it is more preferred to use between approximately 25 to 200 ppm, and, in most circumstances, the use of 130 ppm, measured on an available proton basis, is most desirable. The following example evidences the use of a Lewis acid inhibitor in the practice of the present invention.

EXAMPLE 7

Approximately 59 grams of a 100% cotton rib-knit, three-layered, tubular fabric was combined with approximately 147.5 grams of an α-cyanoacrylate monomer containing composition in a polyethylene bag. The monomer-containing composition was inhibited with 35 ppm of $SO_2$ gas. The α-cyanoacrylate monomer containing composition failed to completely wet the fabric and began an immediate reaction which was evidenced by the observation of hot spots within the polyethylene bag. The areas in which hot spots occurred hardened before the fabric was placed on the patient's appendage.

Approximately 58 grams of a fresh piece of the same fabric was added to a polyethylene bag to which was added 145 grams of α-cyanoacrylate monomer containing composition which had previously been inhibited with 500 ppm $SO_2$. Although the fabric was adequately wet from contact with the monomer-containing composition, the composite failed to harden within 20 minutes and was thus deemed to be unsatisfactory for use herein.

Approximately 60 grams of a fresh piece of the same fabric was again placed in another polyethylene bag to which was added approximately 150 grams of an α-cyanoacrylate monomer containing composition which had been inhibited with 60 ppm $SO_2$ and 60 ppm p-toluene sulfonic acid. The fabric wet well, and there was an approximately 3 minute opportunity available to the user to knead the monomer-containing composition into the fabric to complete the saturation. The resulting product functioned adequately as an immobilizing cast.

As a further preferred embodiment, it is the intent of the present invention to include a plasticizer within the α-cyanoacrylate monomer containing composition. Plasticizers are employed in order to control the hardness of the final cast or splint orthosis and to also enhance the wettability of the fabric support by the polymerizable composition. Suitable plasticizers include mono-functional alaphatic esters such as butyl acetate and butyl cyanoacetate, di-functional alaphatic esters such as dibutylthalate, phosphate esters and phosphonate esters. Further examples include polyethyl cyanoacrylate and polymethyl methacrylate as well as 3,4,5-trihydroxybenzoic acid and its esters are taught in U.S. Pat. No. 4,139,693. These plasticizers can be employed broadly between approximately 0.1 to 25% of the total composition (by weight), while it is more preferable to employ them between 0.5 to 15% (by weight), and most preferable to employ them between 2 to 6% (by weight).

As α-cyanoacrylate monomers can polymerize via the free radical route, to enhance self life it is preferable that a free radical scavenger be included in the composition. Such scavengers include hydroquinone, monoethyl ether of hydroquinone, butylated hydroxy anisole, butylated hydroxy toluene and t-butyl hydroquinone. Hydroquinone is clearly the preferred free radical scavenger for use herein which broadly can be included in the composition between approximately 10 to 500 ppm and, more preferably, 50 to 200 ppm and, most preferably, between 20 to 50 ppm.

Turning more specifically to FIG. 1, illustration is made of a kit of the present invention dedicated to the on-site fabrication of a cas orthosis. The kit is intended to include a bottle of casting gel 5 which includes an α-cyanoacrylate monomer containing composition which further comprises the various plasticizers and free radical scavengers as recited previously.

The kit is intended to further include barrier fabric 7, plastic pouch 8, fabric 3 and, preferably, plastic gloves 9, and elastic bandage 19.

It was previously mentioned that the purpose of the barrier fabric is to somewhat isolate the monomer-containing fabric from the skin of the appendage as cyanoacrylate-containing compositions are somewhat exothermic during polymerization. Also, human skin and hair can easily become bonded to the fabric during polymerization of the monomer. Barrier fabric 7 is intended to protect the patient as well as provide a soft cushioned layer for added comfort and protection as the cast, splint or other orthopedic device may be worn over an extended period of time and can abrade an otherwise unprotected appendage. To further assist in performing this function, barrier fabric 7 should extend beyond hardenable fabric 3 so that the extremities of the barrier fabric could fold over the hardenable fabric, thus cushioning its ends.

In performing these functions, barrier fabric 7 can consist of fabrics composed of fibers of, for example, polyolefins, polynosics, polyacrylics, polyesters, polyamides, polyaramids and polyacetates. Most useful are the polyolefins, polyesters, nylons, acrylics and materials that generally have either a neutral or acid mantle surface to prevent accelerated polymerization of the cyanoacrylate monomer. In fabricating the barrier fabric, it is contemplated that the substantially tubular member be made as a rib-knit, jersey knit, woven fabric, wrap knit or even nonwoven material produced by, for example, needle punch or card web. For spun yarn embodiments, yarn sizes between approximately 0.5/1 cotton count to 100/1 cotton count in single and multiple ends can be used, while it is more preferable to employ between approximately 4/1 to 50/1 cotton count, and most preferable to use 8/1 to 30/1 cotton count. For filament yarns, yarn sizes between approximately 40 denier to 1000 denier in single or multiple ends can broadly be employed, while it is more preferable to use sizes from approximately 75 denier to 600 denier, and most preferable to use between approximately 15 denier to 500 denier in single or multiple count ends.

It was also contemplated as a preferred embodiment that the barrier fabric be treated with material exhibiting high thermal capacitance and low thermal conductivity to fully protect the sensitive user from heat generated to the exothermic polymerization reaction. Such materials are capable of absorbing heat in an isothermal manner and slowly dissipating the isothermal energy as heat at a temperature lower than may otherwise be expected, resulting in added comfort to the patient. In accomplishing this goal, paraffin waxes are used as these materials can absorb heat without having their own temperatures raised in the range of approximately 96 BTUs per pound. Such materials are available from Industrial Raw Materials Corp. sold under the trademark Inderals which have melting points within the range of approximately 108° to 300° F. and, more preferably, between 110° to 160° F. Such paraffin waxes can be used alone or can be modified with microcrystalline wax, butyl rubber or other components such as mineral oils. These materials can be added to the barrier fabric as straight liquid waxes or in solvents such as methylene chloride or perchloroethylene. But most preferred is the application of an emulsion such as described in Example 8.

EXAMPLE 8

Approximately 100 grams of a paraffin wax-based emulsion liquid was prepared having the following ingredients:

| Ingredients | Weight Percentage |
|---|---|
| Wax | 40 |
| Span-60 | 4 |
| Tween-60 | 3 |
| Tween-80 | 1 |
| Methyl Paraben | 0.1 |
| Propyl Paraben | 0.05 |
| Butyl Paraben | 0.05 |
| Water | 51.8 |

The above-recited wax was weighed and brought to its melting point of 117° F. The emulsifiers and preservatives were added to the liquid wax with vigorous stirring as the temperature was brought to 130° F. When the newly constituted composition was in a completely liquid state, water, also at 130° F., was slowly added, and it was noted that the solution converted from a water in oil to an oil in water composition indicated by a decrease in viscosity and a chalky white color. The solution was then cooled to room temperature with stirring to maintain a relatively small particle size distribution.

The above-recited emulsion was applied to barrier fabric 7 through a dip-and-nip pad while maintaining a moderate squeeze on the nip rolls. The fabric was then dried at a temperature of approximately 130° to 140° F. with air flow which resulted in a 90 to 100% dry pickup. It is noted, however, that the emulsion could be applied to the barrier fabric in a pickup range between 50 and 300% by weight and still have a significant impact on skin temperature as measured between the cast or splint surface and underlying skin surface.

EXAMPLE 9

As further illustration of the use of the coated barrier fabric, an approximately 2.8 ounce cotton fabric was wet with approximately 7 ounces of an ethoxyethyl cyanoacrylate monomer-containing resin over a 100% spun polyester rib-knit fabric as a barrier. During polymerization of the monomer, temperatures were recorded at the skin surface in the range of 120° to 124° F.

The above-recited cast fabric coated with the same monomer-containing resin was applied to the same barrier fabric which has now been coated with approximately 200% dry pickup of the wax/solvent solution of Example 7. The recorded skin temperatures during polymerization were in the range of 102° to 103° F.

When paraffin wax emulsions are used, it is contemplated that the present invention be practiced with fabric barriers containing between approximately 20 to 500% dry pickup of the wax and, more preferably, between 50 to 400% dry pickup and, most preferably, between 100 to 300% dry pickup.

Turning again to FIG. 1, illustration is made of the application of the cast of the present invention to a hand, wrist and forearm. In doing so, barrier fabric 7 is first rolled in the shape of a donut and then applied to appendage 21 as shown. It is noted that in such application provision is made for a thumb hole 22. After the barrier fabric has been applied, the medical practitioner should then put on rubber gloves 9 and open plastic bag 8 which, preferably, has been in a sealed state to minimize moisture pickup. The casting gel is then added to the fabric within the plastic bag and kneaded to thoroughly wet the fabric with the α-cyanoacrylate monomer-based resin.

Although fabric 3 can be configured in any shape, such as a tube, flat sheet or tape-like configuration, for use as an immobilizing agent for a typical arm or leg appendage, a tubular design is most preferable. If so, upon removal from the plastic pouch, fabric 3 can again be rolled into the shape of a donut while provision is made for thumb hole 24. Although polymerization has undoubtedly commenced by this point in time, a proper functioning fabric/monomer combination should allow the medical practitioner several minutes to work the cast into the appropriate configuration. It is further noted that the barrier fabric 7 should preferably be provided in a length far exceeding that necessary to underlie the cast fabric so that the ends of the barrier fabric can be brought up over the hardened cast for additional comfort and aesthetic appeal. Optionally, the entire orthosis can be covered with elastic wrap 19.

Components of the splint kit are quite similar to those of the cast. Turning to FIG. 2, it is noted that the splint, like the cast, contains a hardening quantity of α-cyanoacrylate monomer containing resin in bottle 5, barrier fabric 7 outer hardenable fabric 3, elastic or Ace® wrap 19 and rubber gloves 9. Unlike the cast, the splint kit further contains splint cover 30 which, in some instances, could obviate the need for barrier fabric 7.

Turning to its application, one first applies the splint by, in its preferred embodiment, applying optional barrier fabric 7. In the event of a tubular construction, a donut is configured from the barrier fabric after thumb hole 22 has been cut for the hand/wrist/forearm orthosis. Plastic bag 8, again preferably in a sealed condition, containing fabric 3 is opened and the polymerizable monomer-containing composition 5 applied thereto. The fabric is then kneaded to thoroughly work in the resin and wet the fabric which is then removed from bag 8 and applied to splint cover 30 which has been unfolded and laid out on a substantially flat surface. Fabric 3 is then sandwiched by splint cover 30, forming composite 42 which is then molded about the injured appendage. Elastic wrap 19 is then applied to the freshly made splint to "mold" about the appendage. After waiting approximately 5 to 15 minutes or when setting is complete, the wrap can be loosened and re-wrapped for conformance only. It must be emphasized that in view of the use of splint cover 30, barrier fabric 7 may not be needed.

We claim:

1. A method for the application of an orthopedic cast or splint for the immobilization of an appendage comprising applying to a fabric to wet said fabric, a hardening quantity of a composition wherein the hardening component thereof comprises an α-cyanoacrylate monomer and applying the fabric to the appendage which becomes immobilized upon the polymerization of the α-cyanoacrylate monomer wherein the appendage has first been covered with a barrier fabric prior to the application of the α-cyanoacrylate monomer containing fabric in at least those areas to be covered with the α-cyanoacrylate monomer containing fabric.

2. The method of claim 1 wherein said barrier fabric exhibits the properties of high thermal capacitance and low thermal conductivity.

3. The method of claim 2 wherein said barrier fabric comprises a fabric matrix supporting a paraffin wax emulsion.

4. The method of claim 1 wherein said α-cyanoacrylate monomer comprises a compound of the general formula:

wherein $R_1$ is a member selected from the group consisting of alkyl, alkene, alkylalkoxy, furfuryl, aromatic and cycloalkyl groups and mixtures thereof.

5. The method of claim 4 wherein $R_1$ is a member selected from the group consisting of methoxyethyl, ethoxyethyl, isopropoxyethyl, propoxyethyl, t-butoxyethyl, n-butoxyethyl and iso-butoxyethyl and mixtures thereof.

6. The method of claim 1 wherein said α-cyanoacrylate monomer containing composition exhibits a viscosity of from approximately 1 to 3 cps.

7. The method of claim 1 wherein said barrier fabric is comprised of spun yarn having a size between approximately 0.5/1 cotton count to 100/1 cotton count in single or multiple ends.

8. The method of claim 1 wherein said α-cyanoacrylate monomer containing composition further comprises a stabilizer for inhibiting the polymerization of the monomer.

9. The method of claim 8 wherein said stabilizer is employed in a quantity so that polymerization is inhibited to an extent such that the cast remains malleable to approximately 1 to 10 minutes after the application of the fabric containing α-cyanoacrylate monomer containing composition to the appendage.

10. The method of claim 8 wherein said stabilizer comprises a Lewis acid.

11. The method of claim 10 wherein said Lewis acid is a member selected from the group consisting of aromatic sulfonic acid and sulfur dioxide and mixtures thereof.

12. The method of claim 11 wherein said aromatic sulfonic acid comprises p-toluene sulfonic acid.

13. The method of claim 10 wherein said Lewis acid is present in an amount between approximately 25 to 200 ppm measured on an available proton basis.

14. The method of claim 10 wherein said Lewis acid is present in an amount between approximately 20 to 500 ppm measured on an available proton basis.

15. The method of claim 10 wherein said Lewis acid is present in an amount approximately 130 ppm measured on an available proton basis.

16. The method of claim 1 wherein said fabric is comprised of a yarn having a size of approximately 0.5 singles to 100 singles cotton count.

17. The method of claim 1 wherein said fabric comprises a member selected from the group consisting of polynosics, polyesters, polyamides, polyacrylics, polyolefins, polyaramids, carbon and fiberglass.

18. The method of claim 1 wherein said fabric comprises the combination of both a stretch yarn and a nonstretch yarn.

19. The method of claim 18 wherein said stretch yarn is a member selected from the group consisting of textured nylon and textured polyester.

20. The method of claim 19 wherein said stretch yarn is of a size between approximately 1/40 to 1/1000 denier or plies thereof.

21. The method of claim 19 wherein said stretch yarn is of a size between approximately 1/100 to 1/300 denier or plies thereof.

22. The method of claim 18 wherein said stretch yarn is a member selected from the group consisting of natural spandex, natural rubber, synthetic spandex, and synthetic rubber.

23. The method of claim 22 wherein said spandex is of a size between approximately 20 to 1200 denier.

24. The method of claim 22 wherein said rubber is of a size between approximately 200 to 44 gauge.

25. The method of claim 22 wherein said rubber is of a size between approximately 100 to 90 gauge.

26. The method of claim 22 wherein said spandex is of a size between approximately 40 to 70 denier.

27. The method of claim 1 wherein said barrier fabric comprises a member selected from the group consisting of polyolefins, polyesters, polynosics, polyamides, polyacrylics, polyamides, polyaramids and polyacetates.

28. The method of claim 1 wherein said barrier fabric is comprised of spun yarn having a size between approximately 8/1 to 30/1 cotton count in single or multiple ends.

29. The method of claim 1 wherein said α-cyanoacrylate monomer containing composition further comprises a free radical scavenger.

30. The method of claim 29 wherein said free radical scavenger comprises hydroquinone in a quantity between approximately 20 to 150 ppm.

31. The method of claim 29 wherein said free radical scavenger comprises hydroquinone in a quantity between approximately 20 to 60 ppm.

32. The method of claim 1 wherein said α-cyanoacrylate monomer containing composition exhibits a viscosity of from approximately 1 to 20 cps.

33. An orthopedic cast or splint for the immobilization of an appendage comprising a fabric upon which a hardening quantity of a composition wherein the hardening component thereof comprises an α-cyanoacrylate monomer has been applied to wet said fabric wherein upon hardening, the hardened fabric has taken on the shape of the appendage and wherein said α-cyanoacrylate monomer containing composition commences polymerization subsequent to contact with said fabric such that said fabric substantially becomes immobilized within approximately 1 to 20 minutes from the time of application of the α-cyanoacrylate monomer to the fabric.

34. The cast of claim 33 wherein said fabric comprises a member selected from the group consisting of a textile rib knit, a woven fabric, a jersey, a tricot and an interlock knit.

35. The cast of claim 33 wherein approximately 0.1 to 10% by weight of a composition comprising a member selected from the group consisting of cellulose acetate, its homologs, polymethylmethacrylate, ε-polycaprolactone, and mixtures thereof is applied to said fabric.

36. The cast of claim 33 wherein said fabric comprises a member selected from the group consisting of polynosics, polyesters, polyamides, polyacrylics, polyolefins, polyaramids, carbon and fiberglass.

37. The cast of claim 33 wherein said fabric is capable of stretching at least approximately twice its at rest width upon the application of a stretching force being applied thereto.

38. The cast of claim 33 wherein said α-cyanoacrylate monomer containing composition further comprises a free radical scavenger.

39. The cast of claim 38 wherein said free radical scavenger comprises hydroquinone in a quantity between approximately 20 to 150 ppm.

40. The cast of claim 38 wherein said free radical scavenger comprises hydroquinone in a quantity between approximately 20 to 60 ppm.

41. The splint of claim 33 wherein said α-cyanoacrylate monomer containing fabric is configured in the shape of a substantially flat sheet.

42. The splint of claim 41 wherein said α-cyanoacrylate monomer containing fabric is sandwiched within a cover prior to its application to the appendage.

43. The cast of claim 33 wherein said α-cyanoacrylate monomer containing composition further comprises a stabilizer for inhibiting the polymerization of the monomer.

44. The cast of claim 43 wherein said stabilizer is employed in a quantity so that polymerization is inhibited to an extent such that the cast remains malleable for approximately 1 to 10 minutes after the application of the fabric containing α-cyanoacrylate monomer containing composition to the appendage.

45. The cast of claim 43 wherein said stabilizer comprises a Lewis acid.

46. The cast of claim 45 wherein said Lewis acid is present in an amount between approximately 20 to 500 ppm measured on an available proton basis.

47. The cast of claim 45 wherein said Lewis acid is present in an amount between approximately 25 to 200 ppm measured on an avialable proton basis.

48. The splint of claim 45 wherein said Lewis acid is present in an amount approximately 130 ppm measured on an avialable proton basis.

49. The cast of claim 45 wherein said Lewis acid is a member selected from the group consisting of aromatic sulfonic acid and sulfur dioxide and mixtures thereof.

50. The cast of claim 49 wherein said aromatic sulfonic acid comprises p-toluene sulfonic acid.

51. The cast of claim 33 wherein said α-cyanoacrylate monomer containing fabric is configured in the shape of a tube.

52. The cast of claim 33 wherein said fabric is comprised of a yarn having a size of approximately 0.5 singles to 100 singles cotton count.

53. The cast of claim 52 wherein said fabric is comprised of a yarn having a size of approximately 8 singles to 30 singles cotton count.

54. The cast of claim 33 wherein said fabric comprises the combination of both a stretch yarn and a nonstretch yarn.

55. The cast of claim 54 wherein said stretch yarn is a member selected from the group consisting of textured nylon and textured polyester.

56. The cast of claim 55 wherein said stretch yarn is of a size between approximately 1/40 to 1/1000 denier or plies thereof.

57. The cast of claim 55 wherein said stretch yarn is of a size between approximately 1/100 to 1/300 denier or plies thereof.

58. The cast of claim 54 wherein said stretch yarn is a member selected from the group consisting of natural spandex, natural rubber, synthetic spandex, and synthetic rubber.

59. The cast of claim 58 wherein said spandex is of a size between approximately 20 to 1200 denier.

60. The cast of claim 58 wherein said spandex is of a size between approximately 40 to 70 denier.

61. The cast of claim 58 wherein said rubber is of a size between approximately 200 to 44 gauge.

62. The cast of claim 58 wherein said rubber is of a size between approximately 100 to 90 gauge.

63. The cast of claim 33 wherein said α-cyanoacrylate monomer comprises a compound of the general formula:

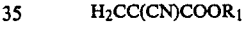

$$H_2CC(CN)COOR_1$$

wherein $R_1$ is a member selected from the group consisting of alkyl, alkene, alkylalkoxy, furfuryl, aromatic and cycloalkyl groups and mixtures thereof.

64. The cast of claim 63 wherein $R_1$ is a member selected from the group consisting of methoxyethyl, ethoxyethyl, isopropoxyethyl, propoxyethyl, t-butoxyethyl, n-butoxyethyl and iso-butoxyethyl and mixtures thereof.

65. The cast of claim 33 wherein said α-cyanoacrylate monomer containing composition exhibits a viscosity of from approximately 1 to 20 cps.

66. The cast of claim 33 wherein α-cyanoacrylate monomer containing composition exhibits a viscosity of from approximately 1 to 3 cps.

67. The cast of claim 33 wherein said fabric is substantially free of water, alcohols and amines prior to the application of the α-cyanoacrylate monomer containing composition.

68. The cast of claim 67 wherein said fabric is subjected to desiccation to remove substantially all water therefrom.

69. The cast of claim 68 wherein a sufficient quantity of a Lewis base remains in said fabric after desiccation such that said cast becomes substantially immobilized in a period between approximately 1 to 20 minutes after the application of said α-cyanoacrylate monomer containing composition.

70. The cast of claim 33 wherein said α-cyanoacrylate monomer containing composition further comprises a plasticizer.

71. The cast of claim 70 wherein said plasticizer comprises a member selected from the group consisting of dioctylphthalate, diisodecylphthalate, polyethylcyanoacrylate and polymethylmethacrylate and mixtures thereof.

72. The cast of claim 70 wherein said plasticizer is present in an amount between approximately 0.10 to 25% by weight based upon the weight of the entire α-cyanoacrylate monomer containing composition.

73. The cast of claim 70 wherein said plasticizer is present in an amount between approximately 2.0 to 6.0% by weight based upon the weight of the entire α-cyanoacrylate monomer containing composition.

74. an orthopedic cast or splint for the immobilization of an appendage comprising a barrier fabric which exhibits the properties of high thermal capacitance and low thermal conductivity and over said barrier fabric a second fabric upon which a hardening quantity of a composition has been applied, said composition having a hardening component comprising an α-cyanoacrylate monomer which has been applied to wet said second fabric wherein upon hardening, the hardened second fabric has taken on the shape of the appendage.

75. The cast of claim 74 wherein said barrier fabric is comprised of spun yarn having a size between approximately 0.5/1 cotton count to 100/1 cotton count in single or multiple ends.

76. The cast of claim 74 wherein said barrier fabric is comprised of spun yarn having a size between approximately 8/1 to 30/1 cotton count in single or multiple ends.

77. The cast of claim 74 wherein said barrier fabric comprises a fabric matrix supporting a parrafin wax emulsion.

78. The cast of claim 74 wherein said barrier fabric comprises a member selected from the group consisting of polyolefins, polyesters, polynosics, polyamides, polyacrylics, polyaramids and polyacetates.

79. A kit for the fabrication of an orthopedic cast or splint for the immobilization of an appendage comprising a barrier fabric configured generally in the shape of said appendage, a second fabric capable of being applied over said appendage in those areas covered by said barrier fabric and a hardening quantity of an α-cyanoacrylate monomer.

80. The kit of claim 79 further comprising a sufficient quantity of an elastic bandage for enclosing said second fabric once it has been applied to the appendage.

81. The kit of claim 79 further comprising a pair of gloves which substantially prevent the penetration of said α-cyanoacrylate monomer containing composition.

82. The kit of claim 79 wherein said second fabric is contained in a substantially air-tight sealed pouch.

83. The kit of claim 82 wherein said second fabric is substantially free of water, alcohols and amines when contained within said pouch.

84. A method for the application of an orthopedic cast for the immobilization of an appendage comprising applying a barrier fabric to said appendage, applying an αcyanoacrylate monomer to a second fabric, applying said second fabric to wet said fabric to said appendage in the areas covered by said barrier fabric and maintaining said appendage in an immobilized state while said α-cyanoacrylate monome polymerizes to harden said second fabric.

85. The method of claim 84 wherein both said barrier fabric and second fabric are configured in the shape of a tube and are applied by rolling each tube into the shape of a donut which is then unrolled onto the appendage.

86. The method of claim 85 wherein said second fabric is covered with an elastic bandage after being applied to the appendage.

87. A method for the application of an orthopedic cast or splint for the immobilization of an appendage comprising applying to a fabric to wet said fabric, a hardening quantity of a composition wherein the hardening component thereof comprises an α-cyanoacrylate monomer and applying the fabric to the appendage which becomes immobilized upon the polymerization of the α-cyanoacrylate monomer, said fabric being comprised of a yarn having a size of approximately 0.5 singles to 100 singles cotton count.

88. The method of claim 87 wherein said fabric is comprised of a yarn having a size of approximately 8 singles to 30 singles cotton count.

89. A method for the application of an orthopedic cast for the immobilization of an appendage comprising applying to a fabric to wet said fabric a hardening quantity of a composition wherein the hardening component thereof comprises an α-cyanoacrylate monomer and applying the fabric to the appendage which becomes immobilized upon the polymerization of the α-cyanoacrylate monomer wherein said fabric is substantially free of water, alcohols and amines by subjecting said fabric to desiccation prior to the application of the α-cyanoacrylate monomer containing composition.

90. The method of claim 89 wherein a sufficient quantity of a Lewis basis remains in said fabric after desiccation such that said cast becomes substantially immobilized in a period between approximately 1 to 10 minutes after the application of said α-cyanoacrylate monomer containing composition.

91. A method for the application of an orthopedic cast or splint for the immobilization of an appendage comprising applying to a fabric to wet said fabric, a hardening quantity of a composition wherein the hardening component thereof comprises an α-cyanoacrylate monomer and further containing a plasticizer comprising a member selected from the group consisting of dioctylphthalate, diisodecylphthalate, polyethylcyanoacrylate, polymethylmethacrylate, and mixtures thereof, and applying the fabric to the appendage which becomes immobilized upon the polymerization of the α-cyanoacrylate monomer.

92. The method of claim 91 wherein said plasticizer is present in an amount between approximately 2.0 to 6.0% by weight based upon the weight of the entire α-cyanoacrylate monome containing composition.

93. The method of claim 91 wherein said plasticizer is present in an amount between approximately 0.10% to 25% by weight based upon the weight of the entire α-cyanocrylate monomer containing composition.

94. A method for the application of an orthopedic cast or splint for the immobilization of an appendage comprising applying to a fabric to wet said fabric a hardening quantity of a composition wherein the hardening component thereof comprises an αcyanoacrylatemonomer, applying the fabric to the appendage and covering said fabric with an elastic bandage whereupon said appendage becomes immobilized upon the polymerization of the α-cyanoacrylate monomer.

95. A method for the application of an orthopedic cast or splint for the immobilization of an appendage comprising applying to a fabric to wet said fabric a hardening quantity of a composition wherein the hardening component thereof comprises an α-cyanoacrylate monomer and applying the fabric to the appendage in the shape of a tube which is rolled out upon the appendage in the area to be immobilized, whereupon the appendage becomes immobilized upon the polymerization of the α-cyanoacrylate monomer.

96. A method for the application of an orthopedic cast or splint for the immobilization of an appendage comprising applying to the fabric to wet said fabric, a hardening quantity of a composition wherein the hardending component thereof comprises an α-cyanoacrylate monomer and applying the fabric to the appendage which becomes immobilized upon the polymerization of the α-cyanoacrylate monomer wherein said fabric is characterized as being capable of stretching at least approximately twice its at-rest width upon the application of a stretching force being applied thereto.

97. A method for the application of an orthopedic cast or splint for the immobilization of an appendage comprising applying to the fabric to wet said fabric, a hardening quantity of a composition wherein the hardening component thereof comprises an α-cyanoacrylate monomer and applying the fabric to the appendage which becomes immobilized upon the polymerization of the α-cyanoacrylate monomer wherein said α-cyanoacrylate monomer containing composition commences polymerization subsequent to contact with said fabric such that said fabric substantially becomes immobilized within approximately 1 to 20 minutes from the time of application of the α-cyanoacrylate monomer to the fabric.

98. A method for the application of an orthopedic cast or splint for the immobilization of an appendage comprising applying to a fabric to wet said fabric, a hardening quantity of a composition wherein the hardening component thereof comprises an α-cyanoacrylate monomer and applying the fabric to the appendage which becomes immobilized upon the polymerization of the α-cyanoacrylate monomer wherein said fabric comprises a member selected from the group consisting of a textile rib knit, a woven fabric, a jersey, a tricot, an interlock knit felt, and paper.

99. A method for the application of an orthopedic cast or splint for the immobilization of an appendage comprising applying to the fabric to wet said fabric a hardening quantity of a composition wherein the hardening component thereof comprises an α-cyanoacrylate monomer and applying the fabric to the appendage which becomes immobilized upon the polymerization of the α-cyanoacrylate monomer wherein said fabric is configured in the shape of a subtantially flat sheet and sandwiched within a cover prior to its application to the appendage.

100. An orthopedic cast or splint for the immobilization of an appendage comprising a fabric upon which a hardening quantity of a composition has been applied wherein the hardening component thereof comprises an α-cyanoacrylate monomer to wet said fabric, said fabric being substantially covered with an elastic bandage after said fabric has been applied to said appendage wherein upon hardening, the hardened fabric has taken on the shape of the appendage.

* * * * *